United States Patent
Tihi et al.

(10) Patent No.: US 8,049,011 B2
(45) Date of Patent: Nov. 1, 2011

(54) PROCESS FOR THE PREPARATION OF LEVOCETIRIZINE AND INTERMEDIATES THEREOF

(75) Inventors: Jaroslav Tihi, Novo Mesto (SI); Rok Zupet, Ljubljana (SI); Anica Pecavar, Novo Mesto (SI); Ivanka Kolenc, Novo Mesto (SI); Darja Pavlin, Straza (SI)

(73) Assignee: KRKA, Tovarna Zdravil, D.D., Novo Mesto, Novo Mesto (SI)

( * ) Notice: Subject to any disclaimer, the term of this patent is extended or adjusted under 35 U.S.C. 154(b) by 87 days.

(21) Appl. No.: 12/530,233

(22) PCT Filed: Mar. 12, 2008

(86) PCT No.: PCT/EP2008/052970
§ 371 (c)(1),
(2), (4) Date: Sep. 8, 2009

(87) PCT Pub. No.: WO2008/110586
PCT Pub. Date: Sep. 18, 2008

(65) Prior Publication Data
US 2010/0105908 A1    Apr. 29, 2010

(30) Foreign Application Priority Data

Mar. 12, 2007 (SI) .................... 200700055
Jul. 30, 2007 (SI) .................... 200700191

(51) Int. Cl.
*C07D 295/00* (2006.01)
(52) U.S. Cl. ......... 544/386; 544/389; 544/390; 544/391
(58) Field of Classification Search ............... 544/386, 544/389, 390, 391
See application file for complete search history.

(56) References Cited

U.S. PATENT DOCUMENTS 5,478,941 A    12/1995    Cossement et al.

FOREIGN PATENT DOCUMENTS

| | | |
|---|---|---|
| EP | 0 617 028 | 6/2000 |
| EP | 0 955 295 | 5/2004 |
| GB | 2 225 321 | * 5/1990 |
| GB | 2225321 | 5/1990 |
| GR | 99100135 | 12/2000 |
| IN | 501/MUM/2004 | 4/2004 |
| JP | 47 031989 | * 11/1972 |
| WO | WO 98/02425 | 1/1998 |
| WO | WO 01/29016 | 4/2001 |
| WO | WO 2004/050647 | 6/2004 |
| WO | WO 2004/065360 | 8/2004 |

OTHER PUBLICATIONS

Clemo et al. (1939) J. Chem. Soc., 1958-1960, "The Optical Rotatory Powers of Some 4-Substituted Benzhydrylamines".
Ingold and Wilson (1933) J. Chem. Soc., 1493-1505, "Optical Activity in Relation to Tautomeric Change. Part I. Conditions underlying the Transport of the Centre of Asymmetry in Tautomeric Systems".
Ip.com (Feb. 16, 2007) IPCOM000146553D, "Polymorphism of levocetirizine".
Schneller et al. (1986) Croatica Chemica Acta, 59(1):307-311, "The Synthesis and Antiviral Properties of 8-Amino-3-[(2-hydroxyethoxy)methyl]-1,2,4-triazolo-[4,3-α]pyrazine".
International Search Report from PCT/EP2008/052970, dated Sep. 18, 2008.

* cited by examiner

*Primary Examiner* — Andrew D Kosar
*Assistant Examiner* — Erich A Leeser
(74) *Attorney, Agent, or Firm* — Swanson & Bratschun, L.L.C.

(57) ABSTRACT

The present invention describes a novel process for the preparation of levocetirizine and pharmaceutically acceptable acid addition salts thereof using diglycolic acid or derivatives thereof and new intermediates used in that process.

10 Claims, 9 Drawing Sheets

PROCESS FOR THE PREPARATION OF LEVOCETIRIZINE AND INTERMEDIATES THEREOF

Related Applications

This application is a 35 U.S.C. §371 national phase application of PCT/EP2008/052970 (WO/2008/110586), filed on Mar. 12, 2008, entitled "New Process for the Preparation of Levocetirizine and Intermediates Thereof," which application claims the benefit of Slovenia Patent Application Serial No. P-200700055, filed on Mar. 12, 2007, and Slovenia Patent Application Serial No. P-200700191, filed on Jul. 20, 2007. Each of these applications is specifically incorporated herein by reference in its entirety.

FIELD OF THE INVENTION

The present invention describes a novel process for the preparation of levocetirizine and intermediates thereof, and its pharmaceutically acceptable salts and esters.

BACKGROUND OF THE INVENTION

Levorotatory [2-[4-[(4-chlorophenyl)phenylmethyl]-1-piperazinyl]ethoxy]acetic acid, also known by the generic name of levocetirizine, has proven useful as a therapeutic agent for the treatment of allergic disease.

Levocetirizine and its salts including its dihydrochloride are known and are effective in the treatment of allergies, including but not limited to, chronic and acute allergic rhinitis, allergic conjunctivitis, pruritus, urticaria and the like. Levocetirizine belongs to the second generation of H1 histamine receptor antagonists, which are believed to offer significant advantages over first generation compounds. Studies have shown that levocetirizine provides safe and effective symptomatic relief of seasonal allergies. Levocetirizine is used also for treating chronic idiopathic urticaria.

GB 2,225,321 describes a process for the preparation of cetirizine in the levorotatory form, dextrorotatory form or a mixture thereof comprising the hydrolysis of enantiomerically pure [2-[4-[(4-chlorophenyl)phenylmethyl]-1-piperazinyl]ethoxy]acetonitrile. Hydrolysis takes place in aqueous, alcoholic or aqueous-alcoholic medium by a base or by an acid; the acid thus obtained is converted to its dihydrochloride. Optically active starting material 1-[(4-chlorophenyl)phenylmethyl]piperazine is obtained by resolution of the corresponding racemic compound, preferably by conversion to its diastereoisomeric salt with tartaric acid. The yield of resolution is rather low, namely only 12.7%. The obtained optically active intermediate is further converted with chloroethoxyacetonitrile in 69% yield.

EP 0 617 028 and EP 0 955 295 disclose a process for the preparation of optically active 1-[(4-chlorophenyl)phenylmethyl]piperazine and its conversion to cetirizine in the levorotatory form or dextrorotatory form or to derivative thereof. The process for the preparation is shown in the following scheme:

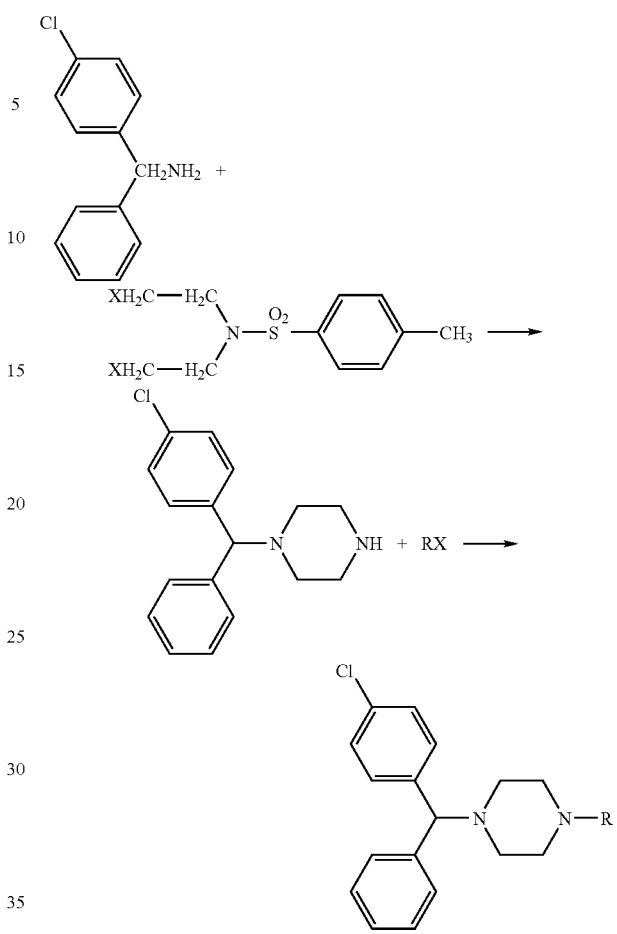

The drawback of the disclosed reaction is that it requires protection of N,N-bis(2-haloethyl)amine, and consequently deprotection of the intermediate obtained.

Preparation of Cetirizine in its Levorotatory Form Proceeds in most known syntheses from enantiomerically pure 1-[(4-chlorophenyl)phenylmethyl]piperazine. Consequently it appears to be very desirable to provide new routes to prepare the enantiomers thereof with improved optical purity and good yields.

Polymorphic form I of crystalline levorotatory dihydrochloride salt of cetirizine and amorphous form thereof are disclosed in WO 2004/050647 and WO 2004/065360. Crystalline form is prepared by crystallization from ketone-containing solvent, such as acetone, methyl ethyl ketone, dimethylketone, 2-pentanone and mixtures thereof. Amorphous form was prepared by solvent evaporation.

There still exists a need for an efficient synthesis of levocetirizine, new intermediates used in the process, suitable for large-scale production.

DESCRIPTION OF THE INVENTION

Figure 1:
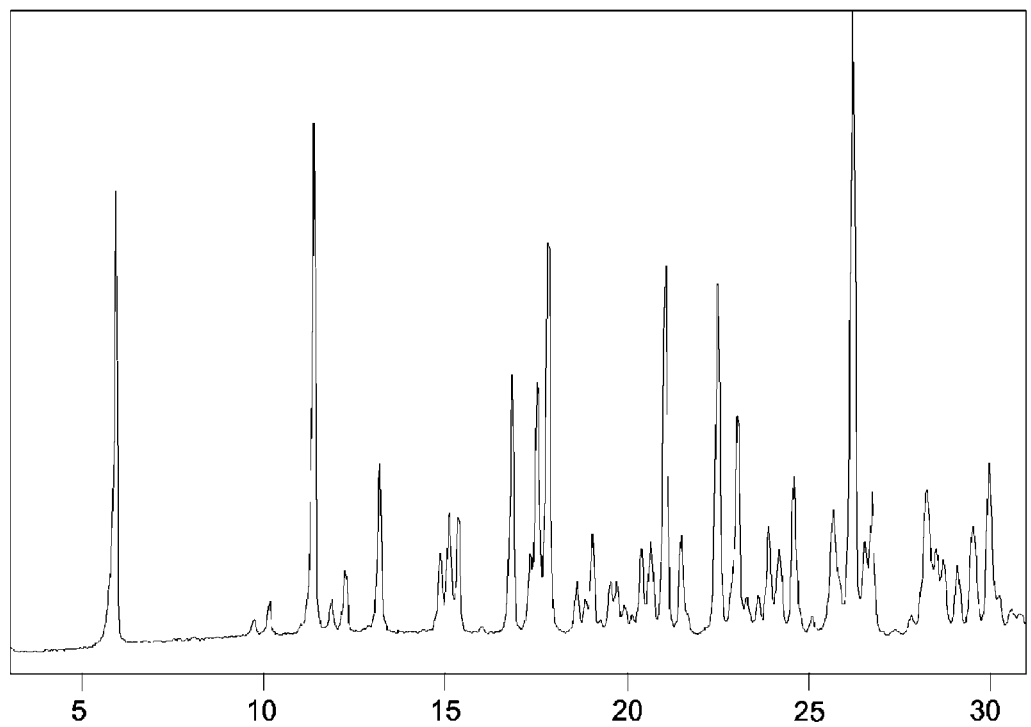
FIG. 1 represents an X-ray powder diffraction pattern of levocetirizine dihydrochloride solvate with acetic acid.
Figure 2:
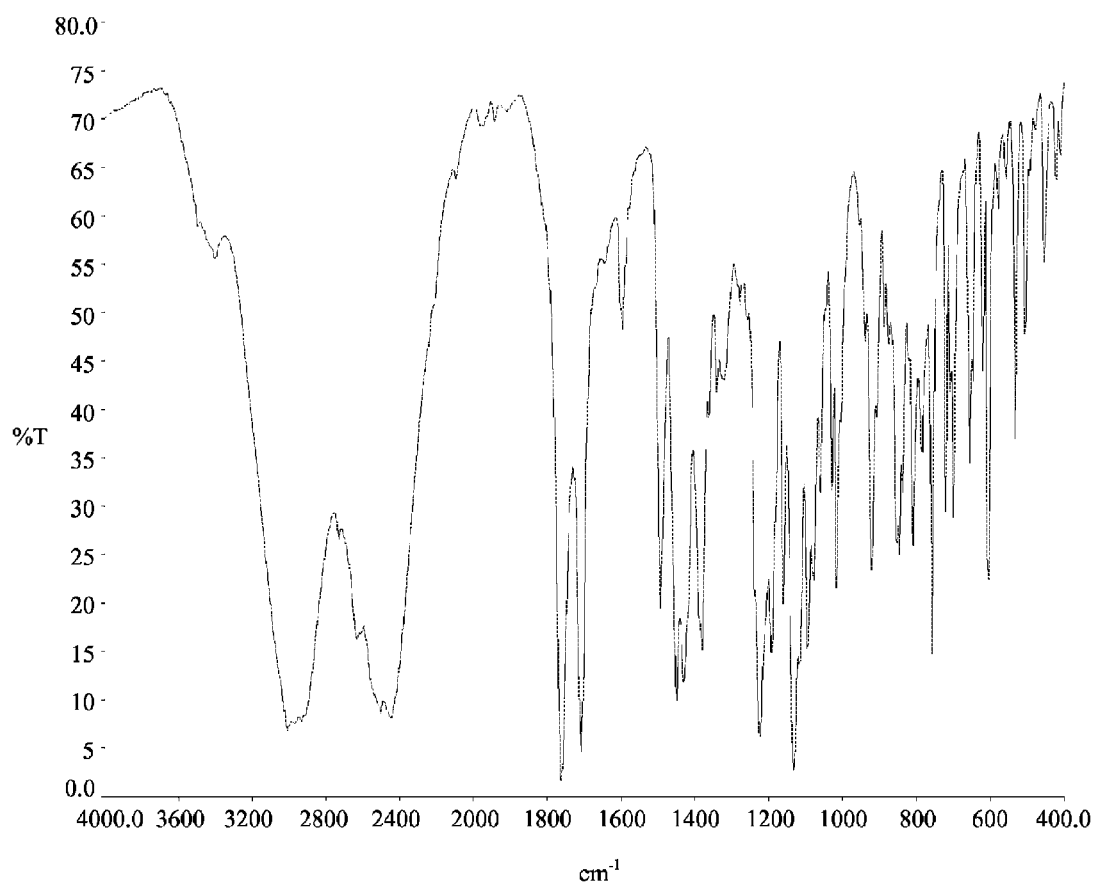
FIG. 2 represents an FT-IR spectrum of levocetirizine dihydrochloride solvate with acetic acid.
Figure 3:
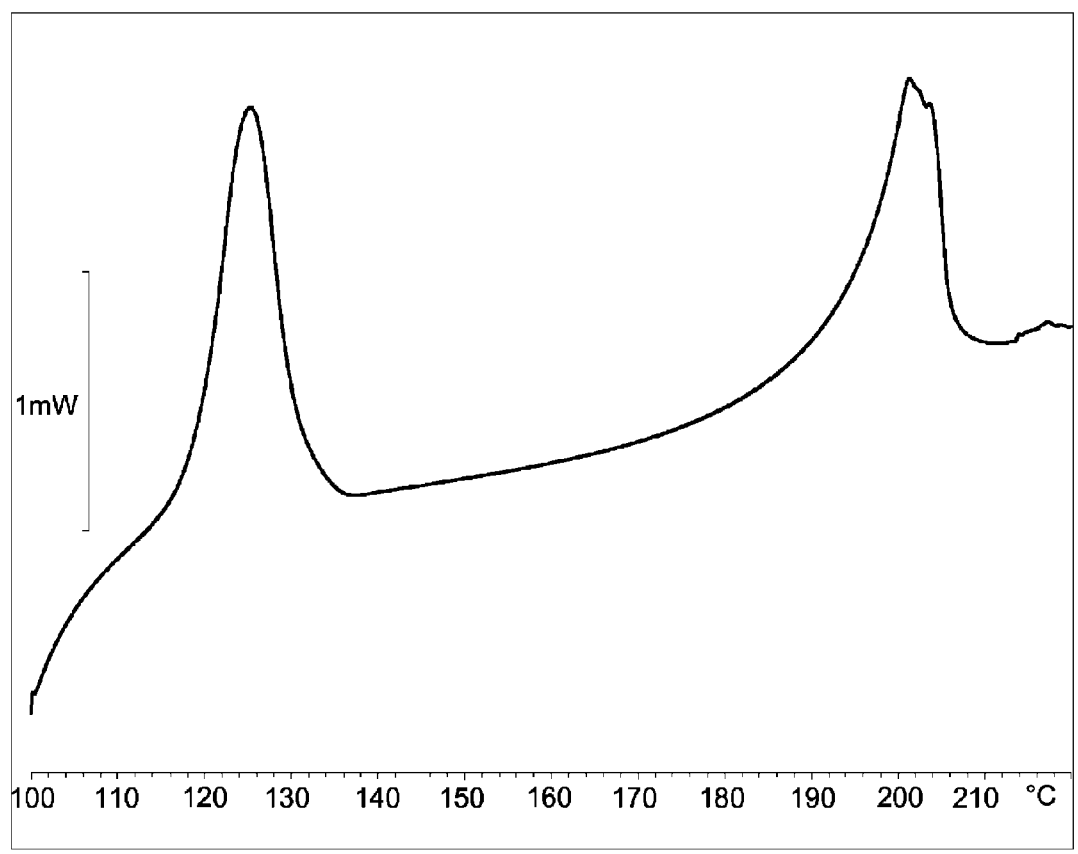
FIG. 3 represents a DSC thermogram of levocetirizine dihydrochloride solvate with acetic acid.
Figure 4:
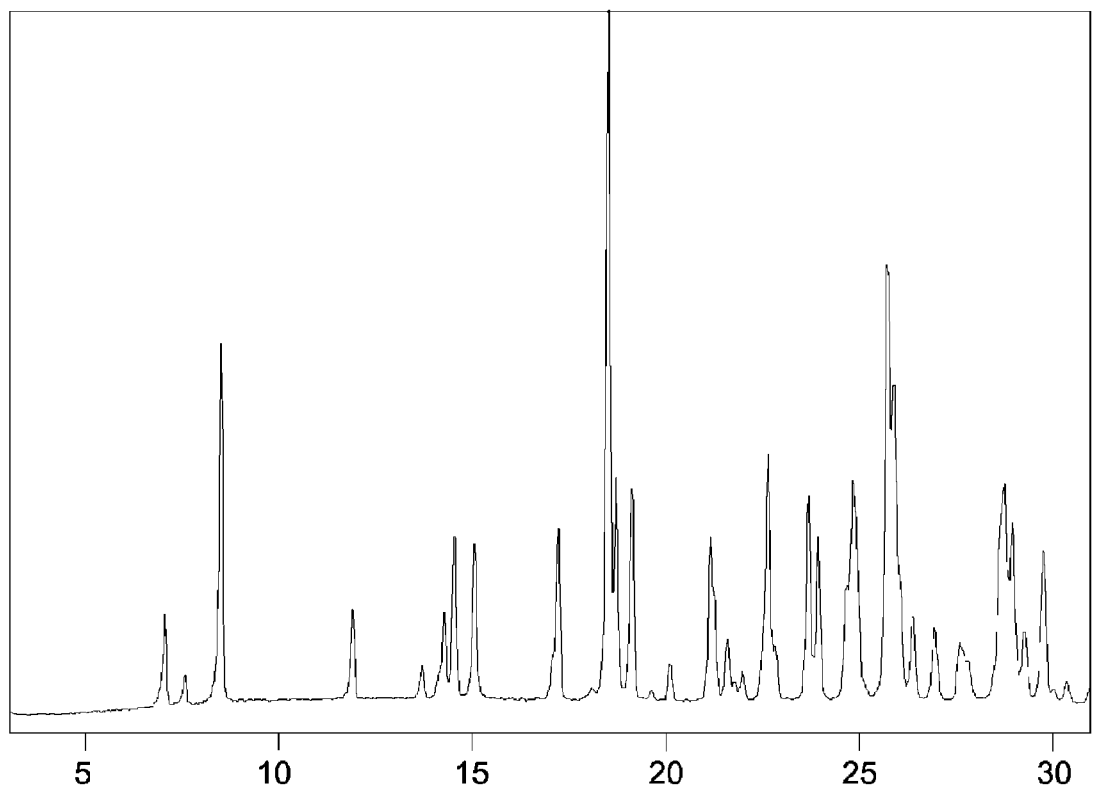
FIG. 4 represents an X-ray powder diffraction pattern of [2-[4-[(4-chlorophenyl)phenylmethyl]-1-piperazinyl]ethoxy]-acetonitrile dihydrochloride.
Figure 5:
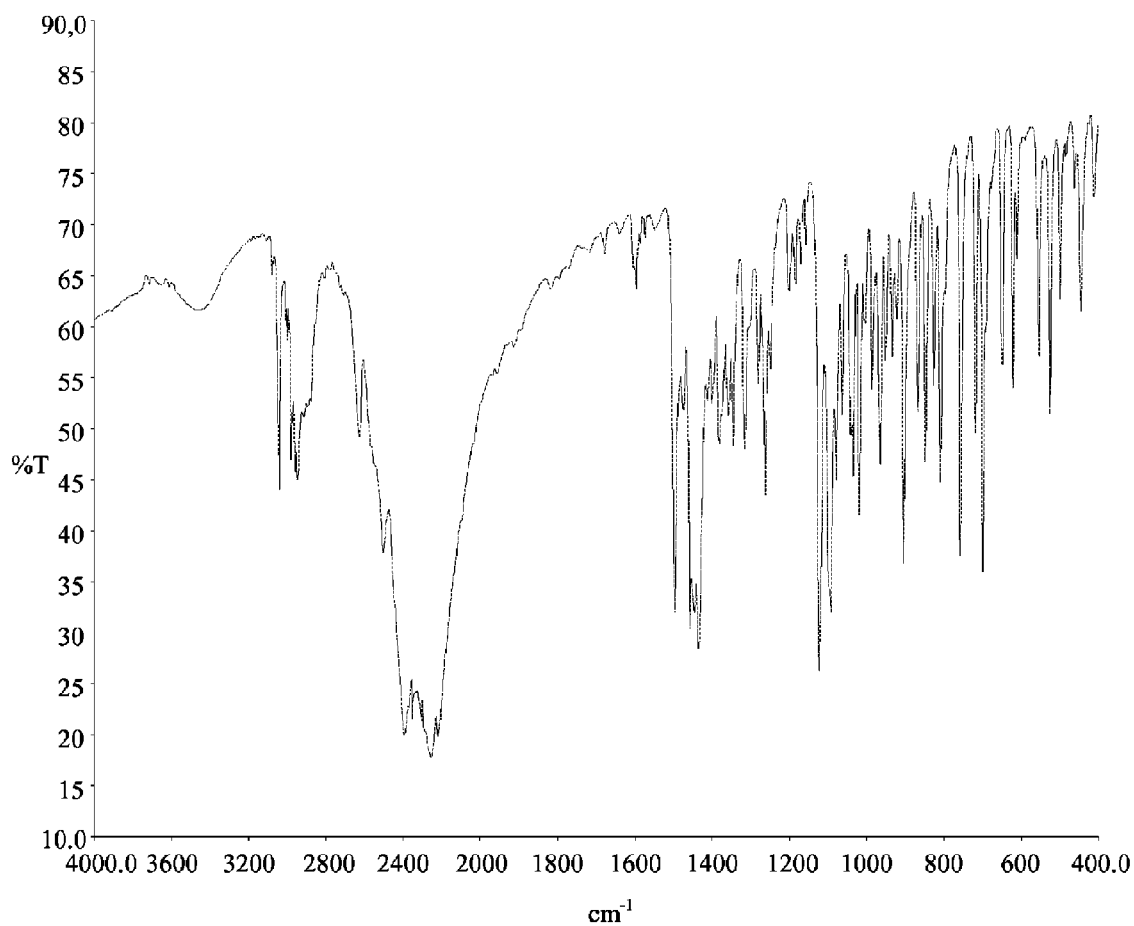
FIG. 5 represents an FT-IR spectrum of [2-[4-[(4-chlorophenyl)phenylmethyl]-1-piperazinyl]ethoxy]-acetonitrile dihydrochloride.
Figure 6:
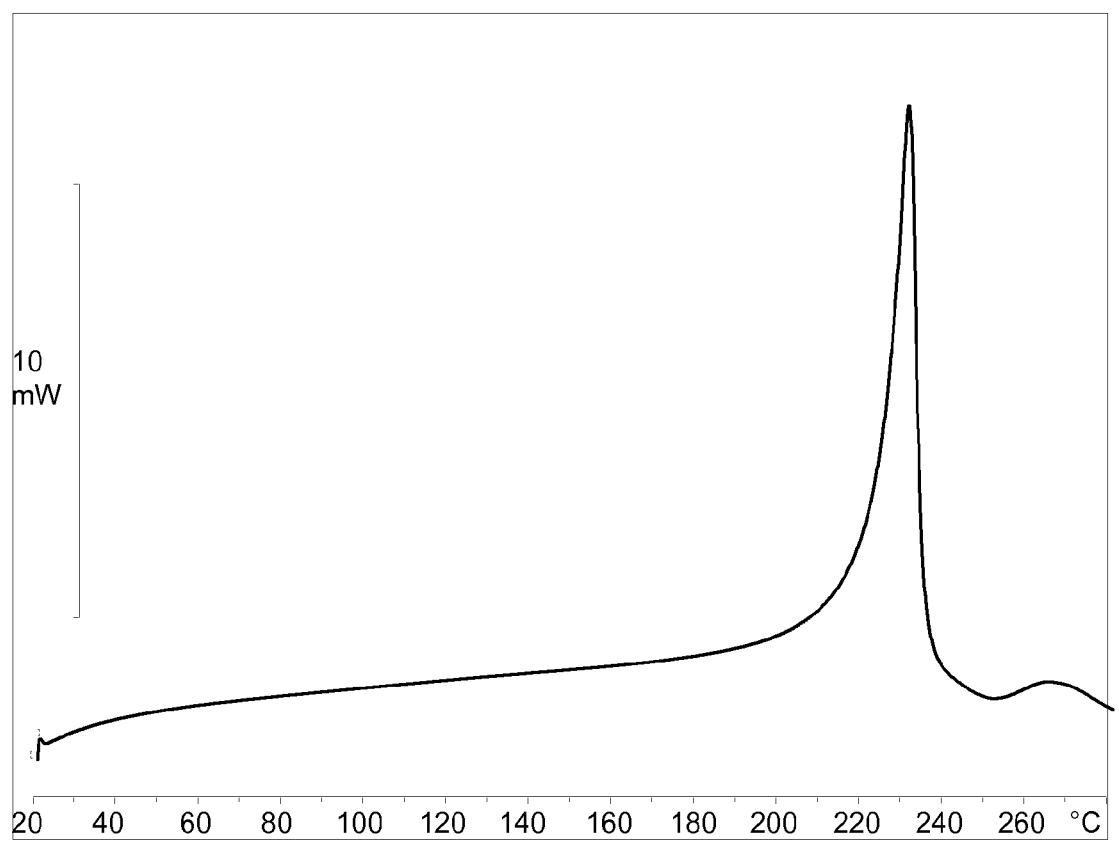
FIG. 6 represents a DSC thermogram of [2-[4-[(4-chlorophenyl)phenylmethyl]-1-piperazinyl]ethoxy]-acetonitrile dihydrochloride.
Figure 7:
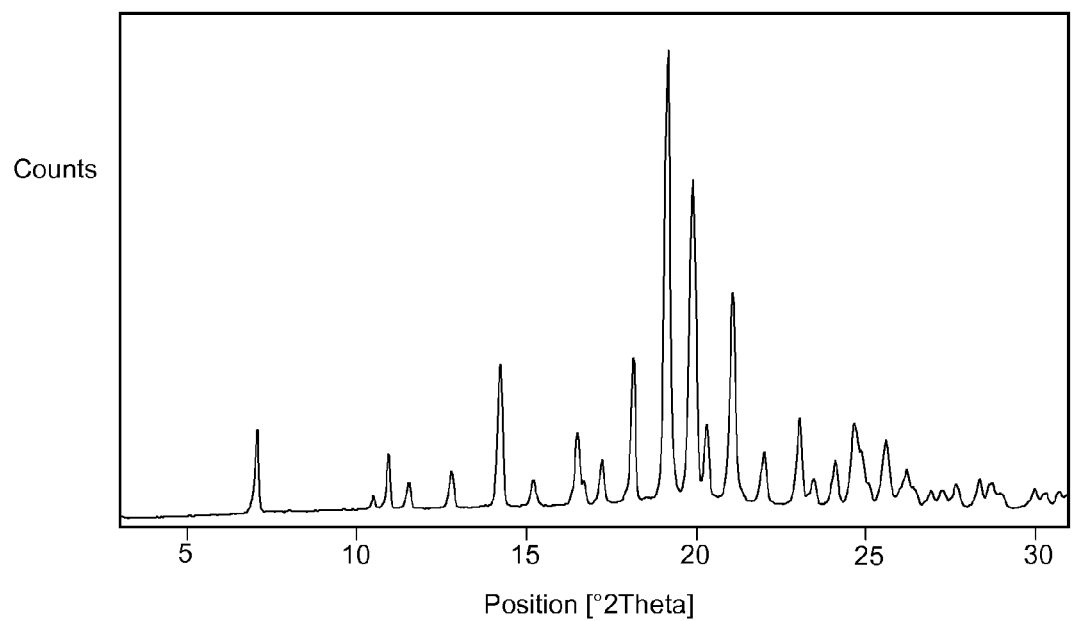
FIG. 7 represents an X-ray powder diffraction pattern of R-2-(2-(4-((4-chlorophenyl)(phenyl)methyl)piperazin-1-yl-2-oxoethoxy)acetic acid.
Figure 8:
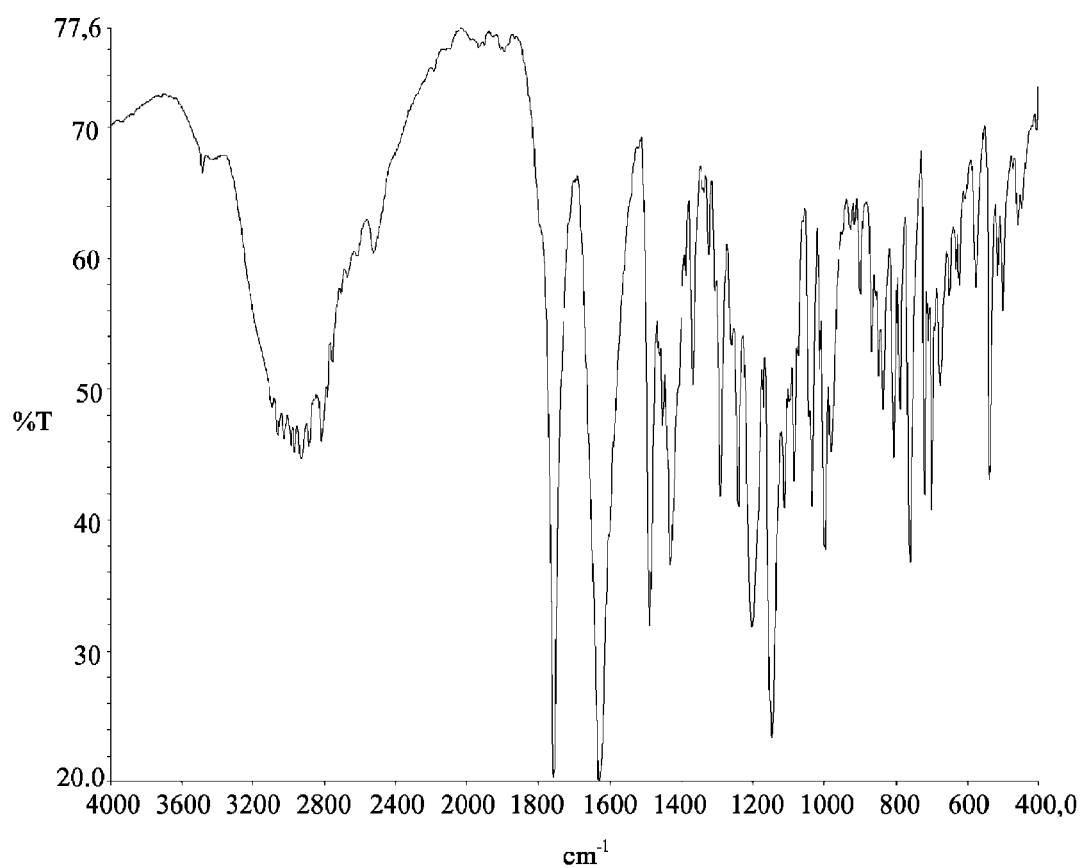
FIG. 8 represents an FT-IR spectrum of R-2-(2-(4-((4-chlorophenyl)(phenyl)methyl)piperazin-1-yl-2-oxoethoxy) acetic acid.
Figure 9:
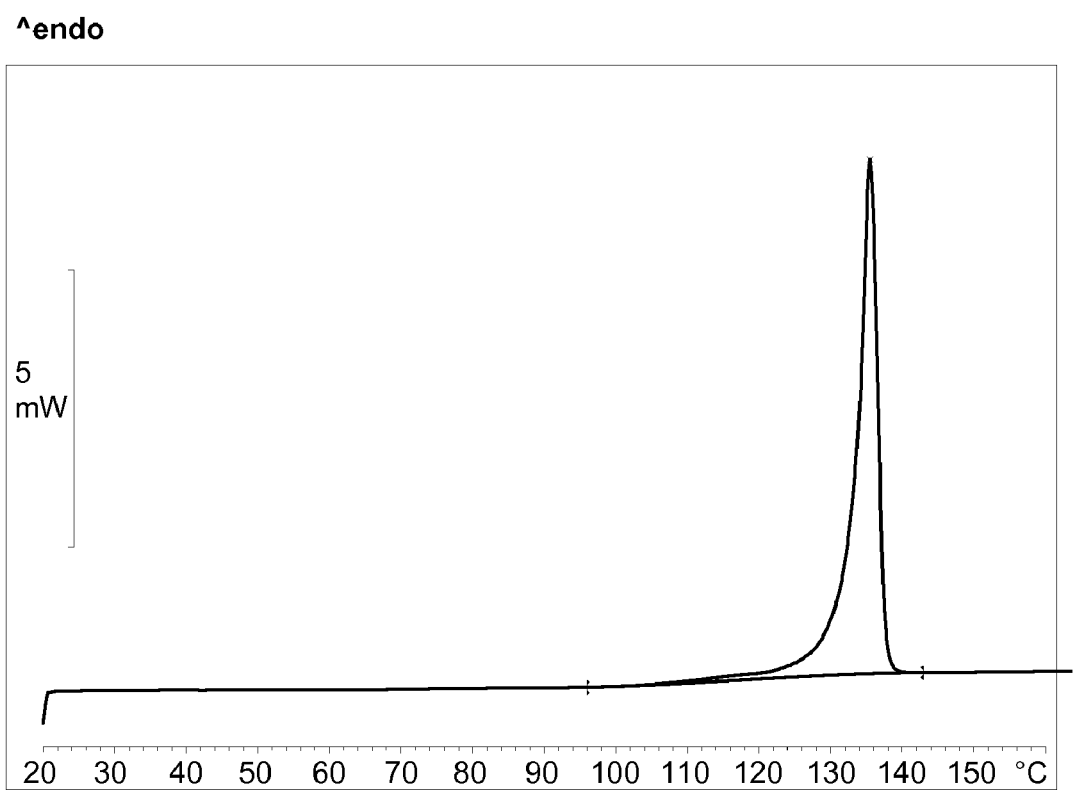
FIG. 9 represents a DSC thermogram of R-2-(2-(4-((4-chlorophenyl)(phenyl)methyl)piperazin-1-yl-2-oxoethoxy) acetic acid.

The present invention provides a new efficient synthesis of levocetirizine and pharmaceutically acceptable salts thereof and new intermediates used in that process.

According to a first aspect, the present invention relates to a process for production of levocetirizine comprising the following steps:

i) reaction of the intermediate of formula II

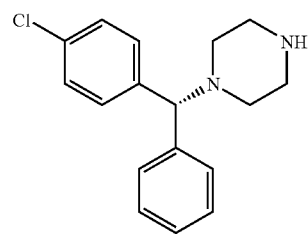

(II)

with a diglycolic acid derivative of formula

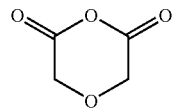

or X—CO—CH$_2$—O—CH$_2$—R, wherein X is OH or halogen group and R is COOH or a group which can be converted to COOH, preferably R is selected from the group consisting of COOH; COX, wherein X is halogen; COOM,
wherein M is alkali or earth alkali metal or N(R$_1$)$_4$; CONH$_2$; CONR$_1$R$_2$, COOR$_1$, CN, CHO, CH$_2$OH or CH(OR$_1$)$_2$, wherein R$_1$ and R$_2$ are independently selected from H, lower alkyl group, aryl group, to obtain intermediate of formula IV

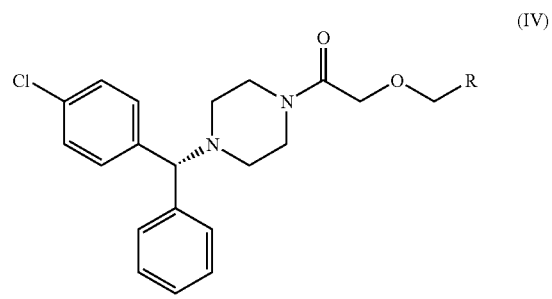

(IV)

wherein R is as defined above;

ii) in case intermediate of formula (IV) wherein R is COOH is obtained, it could be optionally converted to the compound of formula (IV) wherein R is a group which could be converted to COOH;

iii) reducing intermediate of formula (IV) with a selective reducing agent to obtain the product of formula (V)

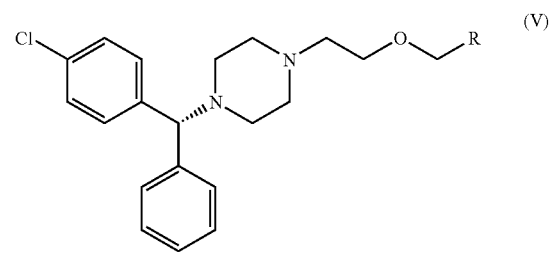

(V)

wherein R is as defined above;

iv) in case R is not COOH, conversion of intermediate (V) to levocetirizine; and v) optionally conversion of levocetirizine to the pharmaceutically acceptable salt thereof.

Glycolic acid derivative can be diglycolic anhydride of formula

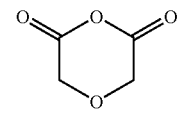

or a derivative of formula X—CO—CH$_2$—O—CH$_2$—R, wherein X is OH or halogen and R is COOH or a group which could be converted to COOH. Preferably, R is selected from the group consisting of COOH; COX, wherein X is halogen; COOM, wherein M is alkali or earth alkali metal or N(R$_1$)$_4$; CONH$_2$; CONR$_1$R$_2$, COOR$_1$, CN, CHO, CH$_2$OH or CH(OR$_1$)$_2$, wherein R$_1$ or R$_2$ are independently selected from H, lower alkyl group and aryl group. The term lower alkyl refers to straight or branched chain saturated aliphatic hydrocarbon radicals having from 1 to 6 carbon atoms, such as methyl, ethyl, isopropyl, tert-butyl etc; or to straight or branched chain aryl substituted alkyl, such as benzyl or triphenylmethyl. The term aryl refers to substituted or unsubstituted aryl groups.

For the preparation of compound of formula (IV) an excess or substantially equimolar amounts of diglycolic acid derivative are employed, preferably 1.5 molar excess, most preferably 1.1 molar excess is employed. The reaction may be carried out in organic solvent, water or mixture thereof. In case water is used as a solvent, the process can be carried out in the presence of a phase transfer catalyst. Suitable organic solvents include polar or non-polar organic solvents such as dimethylformamide, dimethylsulfoxide, acetonitrile; halocarbons such as chloroform, dichloromethane, carbon tetrachloride, 1,2-dichloroethane, and the like; ethers, such as diethyl ether, dioxane, tetrahydrofuran, 1,3-dimethoxyethane and the like, aromatic hydrocarbons such as benzene, toluene, xylene. The reaction may be carried out in the absence of a solvent.

The reaction can also be performed in the presence of tetrabutylammonium chloride, tetrabutylammonium cyanide, tetrabutylammonium fluoride, tetrabutylammonium iodide, tetrabutylammonium hydroxide, tetrabutylphosphonium chloride, tricaprylylmethylammonium chloride, tetraethylammonium chloride, tetramethylammonium bromide, trioctylethylphosphonium bromide, trioctylmethylammonium chloride, trioctylpropylammonium chloride, tetrapropylammonium bromide, tetraphenylarsonium chloride, tetraphenylphosphonium bromide, tetraphenylphosphonium chloride, benzyltrimethylammonium hydroxide, 18-crown-6, dibenzo-18-crown-6, dicyclohexyl-18-crown-6 or mixtures thereof. Preferably, tetra-n-butylammonium bromide or tetra-n-butylammonium iodide is used.

The temperature of the reaction may be from about 0° C. to the boiling point of the reaction mixture, with the range from about 60° C. to boiling point of the reaction mixture being preferred. The reaction time sufficient to substantially complete the reaction is generally from 1 hour to 24 hours.

In carrying out the reaction the reactants are intimately admixed, preferably by adding portionwise while stirring a solution of diglycolic acid or diglycolic acid derivative in a solvent to a solution of the amine of formula (II) also in a solvent, and the mixing is continued with or without the application of heat for the time sufficient to complete the reaction with the formation of the desired product of formula (IV) in the reaction mixture. The product may be recovered or purified by conventional procedures, such as extraction, chromatography or evaporating the solvent in whole or in part by conventional means and recovering the solid or oil which separates out or remains as residue.

The compound of formula (IV) is further reduced with a selective reducing agent to obtain the product of formula (V). Selective reducing agents may be selected from the group consisting of NaBH$_4$ optionally in the presence of carboxylic acids such as acetic acid, trifluoroacetic acid, formic acid or in the presence of sulfonic acids; NaBH$_3$CN optionally in the presence of carboxylic acids such as acetic acid, propanoic acid, trifluoroacetic acid; NaBH$_3$OCOR$_3$ or NaBH(COOR$_3$)$_3$, wherein R$_3$ is methyl, trifluoromethyl and the like; boranes such as borane-solvent complexes, wherein the solvent is selected from tetrahydrofurane (H$_3$B-THF), dimethyl sulfide (H$_3$B—SMe$_2$, BMS), diethyl ether (H$_3$B-diethylether); (R$_4$)$_3$OBF$_4$/NaBH$_4$, wherein R$_4$ is methyl, ethyl, propyl and the like.

The suitable solvent used in the reduction phase is inert organic solvent which may be selected from the group consisting of ethers such as dioxane, tetrahydrofurane, t-butylmethylether, diethylether, diisopropylether, 2-methyltetrahydrofurane; carboxylic acids such as acetic acid; halogenated hydrocarbons; aromatic hydrocarbons. The preferred solvents are THF and dioxane.

Since the relative activity of diborane towards carboxylic acids and amides is similar, it is preferred to protect the carboxylic group by an ester group or an acid halide group. Accordingly, in case boranes are used as a selective reducing agent it is preferred that R in the compound of formula (IV) is other than COOH group.

Typically, the ratio of the reducing agent to the compound of formula (IV) is from 6:1 to 1:1, preferably 3:1 to 1:1, more preferably 1.75:1 to 1:1, most preferably 1.2:1 to 1:1.

The reaction is typically carried out in that way that solution of amide of formula (IV) in a solvent is added to borane solution at temperature from 0° C. to room temperature. The resulting mixture is heated to a temperature of from room temperature to the boiling point of reaction mixture and maintained there for 0.5 hours to several hours to drive the reaction essentially to completion.

After the reaction is completed the product is isolated and purified with conventional means such as extraction and crystallization. Purification by extraction preferably comprises several steps. In the first extraction step alkaline extraction at pH 9-12 is preferably used. For this purpose the reaction mixture is mixed with water and then extracted with halogenated or nonhalogenated water immiscible solvent such as ethyl acetate, methylene chloride or toluene. In the second extraction the pH is preferably adjusted to pH 4-5, more preferably to 4.2-4.8. This step can be performed by using the same solvent system as in the first step, i.e. water/halogenated or nonhalogenated water immiscible solvent such as ethyl acetate, methylene chloride or toluene In case group R in the product of formula (V) is not OH, conversion of intermediate (V) to levocetirizine is performed by processes known in the art.

The compound of formula (II) used as a starting compound according to present invention can be prepared in accordance with the process disclosed in the present invention or any other known process such as disclosed in GB 2,225,321, EP 0 617 028, IN 501/MUM/04.

Another aspect of the invention is a new compound of formula (IV)

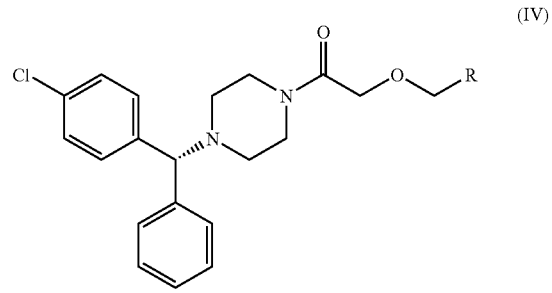

(IV)

wherein R is as defined above. The intermediate of formula (IV) can be used as an intermediate for production of levocetirizine.

Particularly preferred is R-2-(2-(4-((4-chlorophenyl)(phenyl)methyl)piperazin-1-yl-2-oxoethoxy)acetic acid which is characterized by an X-ray powder diffractogram having peaks at about

| No. | Pos. [°2Th.] | d-spacing [A] | Rel. Int. [%] |
|---|---|---|---|
| 1 | 7.1 | 12.48 | 19 |
| 2 | 14.2 | 6.22 | 32 |
| 3 | 16.5 | 5.37 | 17 |
| 4 | 18.2 | 4.88 | 33 |
| 5 | 19.2 | 4.63 | 100 |

-continued

| No. | Pos. [°2Th.] | d-spacing [A] | Rel. Int. [%] |
|---|---|---|---|
| 6 | 19.9 | 4.46 | 71 |
| 7 | 21.1 | 4.21 | 46 |
| 8 | 23.1 | 3.86 | 20 |

Starting compound (II), (−)-1[(4-chlorophenyl)phenylmethyl]piperazine can be prepared in an efficient way by reaction of R-(−)-4-chlorobenzhydryamine and bis(2-haloethyl)amine hydrochloride. It was surprisingly found that no racemisation occurs during that reaction.

The reaction is shown in the following reaction scheme 1.

Reaction scheme 1:

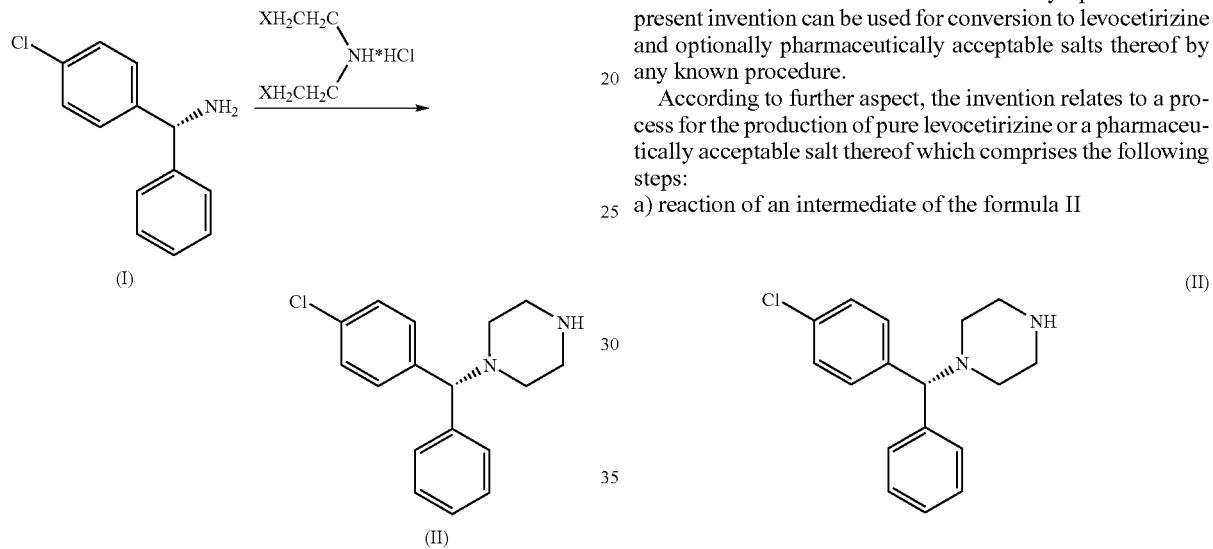

Bis(2-haloethyl)amine hydrochloride can be used, wherein X is chlorine, bromine or iodine atom.

The reaction is typically carried out in the presence of organic base which acts as a solvent and hydrogen chloride scavenger at the same time. Organic bases can be selected from the group consisting of primary, secondary, tertiary alkylamines such as n-ethyldiisopropylamine, triethylamine, diethylamine, butylcyclohexylamine, diisopropylamine, dibutylamine, or heterocyclic amines, such as, pyrrolidine, piperidine, or an alkyl substituted derivative thereof or a mixture thereof. The mixture of various bases can be mixed in any ratio, preferably mixture of n-ethyldiisopropylamine and diethylamine is used in the volume ratio from 1:1 to 1:0.01, most preferably 1:0.08.

The reaction is generally carried out at a temperature of from 50° C. to the reflux of reaction mixture, preferably from 80° C. to the reflux of reaction mixture. The reaction can lasts from 2 hours to 24 hours, preferably from 6 to 8 hours.

The molar ratio between both reagents, namely -(−)-4-chlorobenzhydryamine and bis(2-chloroethyl)amine hydrochloride, can vary from 1:1 to 1:2, preferably 1:1.4 to 1:1.7. It was found out that by using an excess of bis(2-chloro)ethyl amine the yields can be improved.

Typically, after reaction completion, the reaction mixture is concentrated. Water and ethyl acetate are added to the residue. The pH value is adjusted with sodium hydroxide solution to alkaline prior to purification using column chromatography. The pH value of the reaction mixture prior to purification should be more than 9, preferably between 10 and 11.

The reaction is preferably carried out by reaction of -(−)-4-chlorobenzhydryamine with of bis(2-chloroethyl)amine hydrochloride in N-ethyldiisopropylamine in the presence of diethylamine at reflux temperature for several hours, isolation can be made by extraction in a solvent system consisting of water and organic solvent such as ethyl acetate, trichloromethane, dichloromethane to afford crude (−)-1-[(4-chlorophenyl)phenylmethyl]-4-[(4-methylphenyl)sulfonyl]piperazine. The obtained product can be further purified by separation using silica gel chromatography and finally crystallized from hexane to obtain a product with HPLC purity of more than 98%.

The intermediate of formula II obtained by a process of the present invention can be used for conversion to levocetirizine and optionally pharmaceutically acceptable salts thereof by any known procedure.

According to further aspect, the invention relates to a process for the production of pure levocetirizine or a pharmaceutically acceptable salt thereof which comprises the following steps:

a) reaction of an intermediate of the formula II (II)

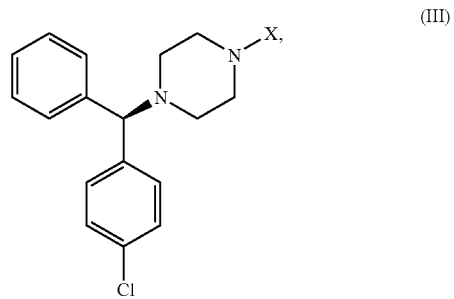

in an aprotic solvent to an intermediate of the formula III or a salt thereof (III)

wherein X is defined as:
—C(=O)—CH₂—O—CH₂—R, wherein R is COOH or a group which can be converted to COOH, or
—CH₂CH₂—O—CH₂—CN, b) conversion of the intermediate III or the salt thereof to a crude levocetirizine or a pharmaceutically acceptable salt thereof, c) purification of the crude levocetirizine or the pharmaceutically acceptable salt thereof to obtain a pure levocetirizine or a pharmaceutically acceptable salt thereof, optionally via formation of a solvate, Preferred groups R are those defined above for the first aspect of the invention.

Preferably, the pure levocetirizine or the pharmaceutically acceptable salt thereof contains less than 0.2% of the intermediate of formula II.

Where the group X in the process described immediately above is —C(=O)—CH$_2$—O—CH$_2$—R, step (b) will typically comprise reducing said group with a selective reducing agent as described above.

Levocetirizine, optionally in the form of pharmaceutically acceptable salt such as dihydrochloride, can be prepared also by a process characterized by the reaction shown in reaction scheme 2:

Reaction scheme 2:

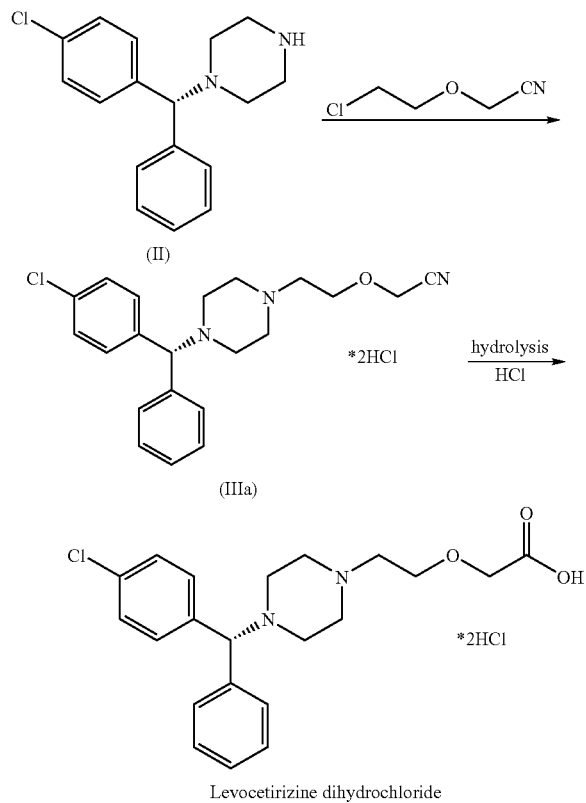

(−)-1-[(4-chlorophenyl)phenylmethyl]-4-piperazine of formula II is reacted with 2-(2-chloroethoxy)acetonitrile in the presence of an acid scavenger, such as an alkali metal carbonate, and optionally in the presence of a small amount of an alkali metal iodide to accelerate the reaction. The reaction can be carried out in an inert solvent, such as an alcohol such as ethanol, n-butyl alcohol, aromatic hydrocarbon such as toluene, xylene, halogenated alkanes such as dichloromethane, nitriles such as acetonitrile. Aprotic solvents are particularly preferred. The most preferred solvent is acetonitrile. By the present invention we found out that the yields of this reaction can be substantially improved by isolating the product [2-[4-[(4-chlorophenyl)phenylmethyl]-1-piperazinil]ethoxy]-acetonitrile of formula IIIa in the form of its hydrochloride. Dihydrochloride form is prepared by introducing gaseous HCl into reaction mixture, or by adding a solution of gaseous HCl in a reaction solvent into the mixture, until pH value reaches value in between 3 to 0.5, preferably below 1, most preferably 1. The reaction carried out in accordance with the present invention proceeds in yields over 90%, preferably 95%.

The reaction does not cause racemization, therefore in case optically pure starting compound is used, optical purity is retained. In this regard, aprotic solvents have been found to be particularly advantageous.

The object of the invention is further also a polymorph form of [2-[4-[(4-chlorophenyl)phenylmethyl]-1-piperazinyl]ethoxy]-acetonitrile dihydrochloride prepared according to the present invention and characterized by X-ray powder diffractogram having peaks at about:

| No. | Pos. [°2Th] | d-values [Å] | Rel. Int. [%] |
|---|---|---|---|
| 1 | 8.5 | 10.4 | 51 |
| 2 | 18.5 | 4.79 | 100 |
| 3 | 19.1 | 4.64 | 31 |
| 4 | 22.7 | 3.93 | 35 |
| 5 | 24.9 | 3.58 | 31 |
| 6 | 25.7 | 3.46 | 63 |
| 7 | 25.9 | 3.44 | 44 |
| 8 | 28.7 | 3.11 | 30 |

It was found that the purity of [2-[4-[(4-chlorophenyl) phenylmethyl]-1-piperazinyl]ethoxy]-acetonitrile of formula IIIa can be improved by maceration in alcohols or ketones at a temperature of from 0° C. to the boiling temperature. Alcohols used for the maceration can be $C_1$-$C_5$-alcohols, preferably methanol and ethanol. Ketones for the maceration can be acetone, MEK or methyl isobutyl ketone. Typically, after completed maceration a product having a chromatographic purity greater than 98% and a content of individual impurity less than 0.2% is obtained.

The reaction proceeds in better yields in case a molar excess of 2-(2-chloroethoxy)acetonitrile is used. Optimal molar ratio between the intermediate of formula II and 2-(2-chloroethoxy)acetonitrile could vary from 1:1.1 to 1:4, preferably from 1:1.5 to 1:3, most preferably from 1:1.5 to 1:2.

The reaction is performed at a temperature between 60 and 200° C., preferably at a temperature between 80 and 120° C., for approximately 7 to 24 hours, as shown in Scheme 2.

2-(2-chloroethoxy)acetonitrile can be prepared in any way known in the art such as Suomen Kemistilehti (1944), 17 B, 17-19, Croatica Chemica Acta (1986), 59(19), 307-11. The HPLC purity of 2-(2-chloroethoxy)acetonitrile entering into reaction should be of least 95%.

Nitrile intermediate IIIa is hydrolyzed either by basic or acidic hydrolysis or by enzyme-catalysed hydrolysis.

In case of basic hydrolysis the nitrile intermediate of formula IIIa is heated at the temperature from 20° C. to 110° C., preferably from 60 to 90° C., in the presence of an inorganic base such as an alkali metal hydroxide in a solvent selected from water or alcohol, such as methanol, ethanol, propanol, 2-propanol, or a mixture thereof. Preferably, as alkali metal hydroxide KOH or NaOH is used and as a solvent a mixture with methanol or ethanol is used. Most preferably, KOH in methanol/water mixture is used.

During our work we found out that an excess of alkali metal hydroxide can cause racemisation. Therefore, the most optimal weight ratio of alkali metal hydroxide to the intermediate of formula IIIa would be from 1:1 to 4:1, preferably 1.5:1 to 3:1.

Levocetirizine formed is present in the reaction mixture in the form of alkali metal salt, from which the acid is liberated by acidification of the reaction mixture by means of an inorganic acid, preferably hydrochloric acid. Levocetirizine acid is then extracted by means of an organic solvent such as dichloromethane, toluene, ethylacetate, preferably dichloromethane. We found out that the pH value of the water solution prior to extraction may influence extraction yields. Thus, it should be maintained between 4 and 5, preferably between 4.2 and 4.8.

After the completed extraction the levocetirizine can be converted to the levocetirizine dihydrochloride by introducing HCl gas into the dichloromethane extract. For better yield and quality of product, dichloromethane may be evaporated and the residue dissolved in another solvent such as an alcohol, an aromatic hydrocarbon, an ester, an ether or a ketone. Preferred solvents are toluene, ethyl acetate, propyl acetate, isopropyl acetate, butyl acetate and acetone. The most preferred solvent is acetone. For the precipitation, HCl gas or acetone saturated with HCl gas is introduced into this solution.

Typically, the disclosed process for basic hydrolysis gives yields of above 90%, with the obtained product HPLC (area) purity being above 98% or even above 99%.

In case of acidic hydrolysis, the intermediate of formula IIIa is heated in the presence of an inorganic acid, such as hydrochloric acid, preferably in an aqueous medium, at a temperature between 60° C. and the reflux temperature of the reaction mixture. Levocetirizine acid is then extracted from the reaction mixture by means of an organic solvent such as dichloromethane, toluene, ethylacetate, preferably from dichloromethane.

The free levocetirizine acid is then converted into the dihydrochloride salt by dissolving it in a ketone solvent and introducing HCl in gaseous form into the reaction mixture and/or by introducing a solution of HCl gas in a reaction solvent, until the pH reaches a value between 0.5 to 3, preferably 0.5 to 1. The ketone solvent may be selected from the group of acetone, methyl ethyl ketone, diisobutyl ketone, dissopropyl ketone, preferably acetone.

The obtained salt can exist in polymorphic form disclosed in WO2004/050647 or IPCOM 000146553D.

Levocetirizine dihydrochloride can be additionally recrystallized from a solvent/antisolvent mixture. As a solvent carboxylic acid or water and as an antisolvent ketone, ester or ether can be used. A preferred solvent is acetic acid or water, and a preferred antisolvent is acetone, ethyl acetate, isopropyl acetate or butyl acetate. Most preferably, as solvent acetic acid and as antisolvent acetone is used. The purity of the product obtained is greater than 99.5%. The X-ray powder diffractogram of thus obtained levocetirizine dihydrochloride solvate with acetic acid has the following peaks at about:

| No. | Position [°2Th.] | d-values [Å] | Rel. Int. [%] |
|---|---|---|---|
| 1 | 5.9 | 14.9 | 72 |
| 2 | 11.4 | 7.77 | 81 |
| 3 | 16.8 | 5.29 | 42 |
| 4 | 17.5 | 5.06 | 41 |
| 5 | 17.8 | 4.97 | 64 |
| 6 | 21.1 | 4.22 | 59 |
| 7 | 22.5 | 3.95 | 58 |
| 8 | 26.2 | 3.40 | 100 |

It is important to control the size of the particles of levocetirizine dihydrochloride during its preparation. The average particle size of particles prepared is 5 to 200 μm, preferably between 20 and 150 μm. If unstirred, crystallization from organic solvents might also yield bigger particles, e.g. with an average diameter of above 200 μm which need to be milled or processed in any other way which reduces particle size, prior to their application in pharmaceutical formulations. When milling, particles of less than 3 μm average diameters may be produced. For this purpose air jet mills, ball mills or hammer mills are commonly used as milling equipment. However, it is not enough to control only the average size of particles, but also the particle size distribution.

Average particle size and particle size distribution is important to assure that the technological process is industrially applicable, i.e. does not cause segregation of ingredients of tabletting mixture if it is not tabletted/compressed just after preparation of tabletting mixture.

The present invention is illustrated by the following Examples without being limited thereto.

EXAMPLES

Example 1

(−)-1-[(4-chlorophenyl)phenylmethyl]-4-piperazine

Charge 300 mL of N-ethyldiisopropylamine, 30 g of -(−)-4-chlorobenzhydryamine (Clemo, J. Chem. Soc. (1939) 1958-1969; Ingold, J. Chem. Soc. (1933) 1493-1505) and 42 g of bis(2-chloroethyl)amine hydrochloride in a reaction vessel, stir and heat to reflux for 3 hours. Cool to 60° C., add 24 mL of diethylamine, then heat the mixture again reflux temperature for another 5 hours. After reaction is completed evaporate the solvent in vacuum, add a mixture of water and ethyl acetate (1:1), adjust aqueous phase pH value to 10-11 with 30% sodium hydroxide solution. Separate organic phase and extract aqueous phase with ethyl acetate. Wash combined organic phase with purified water, decolorize organic phase with activated carbon, and evaporate the filtrate in vacuum. Separate impurities by of silica gel chromatography by eluting with ethyl acetate/ethanol (7:1) and/or then with ethyl acetate/ethanol/ammonia (7:1:0.25). Collect the eluate and evaporate the solvent in vacuum to obtain the oily residue which is further dissolved in hexane, treated with activated carbon heated and filtered. Cool the filtrate to 10° C. for 1 hour, collect a precipitate and dry at 40-45° C. in vacuum for 5-8 hours to afford a product. HPLC (area) 98-99%.

Example 2 a) [2-[4-[(4-chlorophenyl)phenylmethyl]-1-piperazinil]ethoxy]-acetonitrile dihydrochloride Charge 2400 mL of acetonitrile to the reaction vessel, add 400 g of (−)-1-[(4-chlorophenyl)phenylmethyl]-4-piperazine, 300 g $Na_2CO_3$, 20 g KI and 300 g of 2-(2-chloroethoxy) acetonitrile in turn under stirring.

Stir and gradually raise the temperature to 110-115° C. Keep the temperature for 20 hours, after the reaction is completed, cool the mixture to 80-90° C. and add 25 g of activated carbon and stir for 20 minutes. Filter off carbon and wash cake with appropriate amount of acetonitrile. Into combined filtrate introduce dry HCl gas until pH value reaches 0.5-1. Continue to stir the slurry for 20 minutes and filter. Wash the cake with appropriate amount of ethanol and dry at 50-55° C. for 10 hours to obtain 520 g of the title product.

The yield 95%, HPLC (area) 95%. The obtained [2-[4-[(4-chlorophenyl)phenylmethyl]-1-piperazinyl]ethoxy]-acetonitrile dihydrochloride has in the X-ray powder diffractogram the peaks at about: 8.5; 18.5; 19.1; 22.7; 24.9; 25.7; 25.9 in 28.7±0.2° 2Theta.

b) Maceration of a crude [2-[4-[(4-chlorophenyl)phenylmethyl]-1-piperazinyl]ethoxy]-acetonitrile dihydrochloride 10 g of [2-[4-[(4-chlorophenyl)phenylmethyl]-1-piperazinyl]ethoxy]-acetonitrile dihydrochloride were suspended in 30 mL of methanol. The suspension was heated to the boiling temperature and stirred at this temperature for at least 20 minutes. Thereafter the suspension was cooled to 0° C. and stirred at this temperature for one hour. The precipitate was filtered, washed with cold methanol and dried. HPLC (area) 98%.

Example 3

Levocetirizine 3000 mL of methanol and 300 g of [2-[4-[(4-chlorophenyl)phenylmethyl]-1-piperazinyl]ethoxy]-acetonitrile dihydrochloride were added into a reaction vessel and thereto a KOH solution prepared with 600 g of KOH and 600 mL of purified water was added under stirring and keeping the reaction temperature below 40° C. The temperature was gradually raised to 70-76° C. and kept for 24 hours. After the reaction was completed, the reaction mixture was cooled to 40-45° C. and methanol was distilled off at a reduced pressure. Then 1000 mL of purified water and 3000 mL of $CH_2Cl_2$ were added and the temperature was decreased to 20-30° C. pH value was adjusted to 4.2-4.8 with 37% HCl. The organic layer was separated and the water layer was extracted twice more with 2000 mL of $CH_2Cl_2$.

The organic phases were combined, dried with 200 g of anhydrous sodium sulfate for one hour and filtered. The organic phase was concentrated until an oily residue was obtained, which was dissolved in 3 L of acetone. To the acetone solution a dry HCl gas was introduced until pH reached the value of less than 1. The reaction mixture was heated to 60° C. and refluxed for 20 minutes. It was cooled to 30-35° C. and then filtered and the cake was washed with 1 L of acetone. Then it was dried at 50-55° C. under reduced pressure (−0.08~−0.1 MPa) for 8 hours. 280 g of levocetirizine dihydrochloride were obtained.

Example 4

R-2-(2-(4-((4-chlorophenyl)(phenyl)methyl)piperazin-1-yl-2-oxoethoxy)acetic acid Alternative A 2 g of R-1-((4-chlorophenyl)(phenyl)methyl)piperazine and 0.88 g of diglycolic acid anhydride was dissolved in 107 mL of acetonitrile. The reaction mixture was refluxed for 12 h. After the reaction was completed the solvent was evaporated and the obtained residue dissolved in 20 mL water with addition of 2 mL of 1M NaOH and then 10 mL of dichloromethane was added. The suspension was stirred for 20 minutes and the organic phase was separated. To the aqueous phase another portion of 10 mL of dichloromethane was added, pH of suspension is adjusted at 4.5 to 5. Aqueous phase was extracted twice again with 2×10 mL of dichloromethane. Organic phases were collected, dried over anhydrous sodium sulfate, filtrated and evaporated. The obtained crude product could be used in the next step without further purification.

Alternative B 2 g of R-1-((4-chlorophenyl)(phenyl)methyl)piperazine and 0.88 g of diglycolic acid anhydride was dissolved in 10 ml of dimethylsulfoxide. To the solution 20 ml of tetrabutylammmonium bromide was added. The solution was stirred for another hours until the reaction was completed. The solution was diluted with 67 ml of water and 15 ml of isopropyl acetate was added. The phases were separated and water layer was reextracted with isopropyl acetate. Organic layer was mixed with demineralised water (40 ml) and pH of suspension was adjusted to 10 with 2M NaOH. The layers were separated and to the water phase 40 ml of isopropyl acetate was added. pH of suspension was adjusted to 3.5. The layers were separated and water phase was reextracted twice with isopropylacetate. Organic phase was rinsed with water and evaporated to dryness. 2.5 g of product (HPLC (area) is 98.5%)) was crystallised. The product was dried at vacuum at 50° C.

Example 5

Levocetirizine Dihydrochloride

Oily product from the previous step was dissolved in 20 mL dioxane, to the solution 1.3 g of $NaBH_4$ was added. The suspension was cooled to 10° C. and during intensive stirring 2.1 g of acetic acid in 7 mL dioxane was added. The reaction mixture was refluxed for two hours, cooled to room temperature and the solids were filtered off. The filtrate was evaporated, to the residue 20 mL water was added and pH was adjusted to 5. The aqueous phase was extracted three times with 10 mL of dichloromethane. Organic extracts were combined, dried over anhydrous sodium sulfate and the solvent was removed at a reduced pressure. The obtained crude levocetirizine was dissolved in 10 mL acetone and 2 mL of 36% HCl was added and stirred for one hour. The product is filtered off and dried.

Example 6

1 g of product of R-2-(2-(4-((4-chlorophenyl)(phenyl)methyl)piperazin-1-yl-2-oxoethoxy)acetic acid was dissolved in 10 ml of dry tetrahydrofurane at 0° C. During intensive stirring 0.23 ml of oxalylchloride was added dropwise. After half an hour when the conversion of acid to acid chloride was completed 0.8 ml of dimethylsulphide borane complex (10 M calculated on $BH_3$) was added in three portion. After the reaction was completed, the reaction mixture was poured in water (250 ml) and additionally stirred for half an hour. To the suspension 100 ml of ethyl acetate was added, pH was adjusted to 10 and the phases were separated. To the water phase 100 ml of methylene chloride was added, pH was adjusted with concentrated hydrochloric acid to 4.2 and phases were separated: the organic layer was rinsed with water, dried with sodium sulphate and evaporated to dryness. The oil residue was dissolved in 30 ml of acetone and HCl gas was introduced until pH reached the value of less than 1. The reaction mixture was heated to 60° C. and refluxed for 20 minutes. It was cooled to 30-35° C. and then filtered and the cake was washed with 20 ml of acetone. Then it was dried at 50-55° C. under reduced pressure (−0.08~−0.1 MPa) for 8 hours. 720 mg of levocetirizine dihydrochloride were obtained.

Example 7

Recrystallization of Levocetirizine Dihydrochloride 75 g of levocetirizine dihydrochloride with 0.17% content of compound II were dissolved in 225 mL of acetic acid at 80°

C. The solution was cooled to 50° C. and at this temperature 562 mL of acetone were gradually added within 1.5 hour. After addition of acetone the suspension was cooled to 0° C. and stirred at this temperature for at least 1 hour. The product, levocetirizine dihydrochloride was filtered off. The product was dried in vacuum dryer at 50° C. There were obtained 58 g of the product, which HPLC purity (area) was 99.9%. The content of compound II was under the detection limit, which was 0.005%.

Analysis method: HPLC; column RP18; phosphate buffer (pH 7), acetonitrile/methanol; gradient method; UV detector, 230 nm.

Example 8

Preparation of Levocetirizine Dihydrochloride Solvate with Acetic Acid 50 g of levocetirizine dihydrochloride were suspended in 100 mL of acetic acid and heated until the substance dissolved. Then it was cooled slowly under stirring to 50° C. until the suspension appeared and after that at this temperature 100 mL of acetone were added to the suspension. After the addition of acetone the suspension was cooled to a room temperature, the precipitate was filtered off and the product was washed with acetone. The product was dried in vacuum dryer at 50° C. There were obtained 43.1 g of the product with HPLC purity (area) 99.9%.

Analysis method: HPLC; column RP18; phosphate buffer (pH 7), acetonitrile/methanol; gradient method; UV detector, 230 nm.

Example 9

Preparation of Levocetirizine Dihydrochloride from Levocetirizine Dihydrochloride Solvate with Acetic Acid 10 g of levocetirizine dihydrochloride solvate with acetic acid were suspended in 60 mL of aceton and stirred at room temperature for one hour. After one hour the suspension was filtered off and the filter cake was washed with acetone and dried in vacuum dryer. The weight of a dry product was 8.9 g. HPLC purity (area) was 99.9%.

The invention claimed is:

1. A process for the production of levocetirizine, or a pharmaceutically acceptable salt thereof, comprising the steps:

a) reaction of an intermediate of the formula II

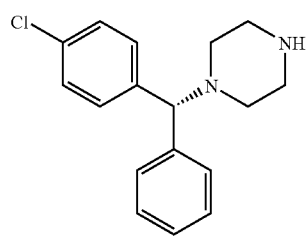

(II)

to an intermediate of the formula III or a salt thereof

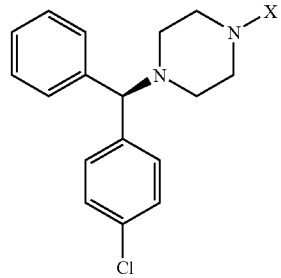

(III)

wherein X is —C(═O)—CH$_2$—O—CH$_2$—R, wherein R is COOH; COX, wherein X is halogen; COOM, wherein M is alkali or earth alkali metal or N(R$_1$)$_4$; CONH$_2$; CONR$_1$R$_2$, COOR$_1$, or CN, wherein R$_1$ and R$_2$ are independently selected from H, lower alkyl group, aryl group;

b) conversion of the intermediate III or the salt thereof to levocetirizine or a pharmaceutically acceptable salt thereof.

2. The process of claim 1, comprising the following steps:

a) reaction of an intermediate of the formula II

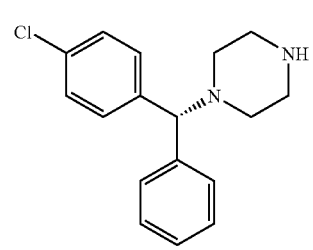

(II)

in an aprotic solvent to an intermediate of the formula III or a salt thereof

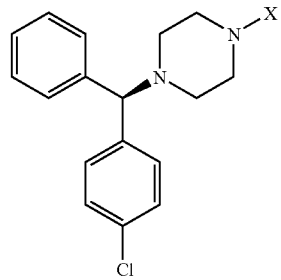

(III)

wherein X is —C(═O)—CH$_2$—O—CH$_2$—R, wherein R is COOH; COX, wherein X is halogen; COOM, wherein M is alkali or earth alkali metal or N(R$_1$)$_4$; CONH$_2$; CONR$_1$R$_2$, COOR$_1$, or CN, wherein R$_1$ and R$_2$ are independently selected from H, lower alkyl group, aryl group;

b) conversion of the intermediate III or the salt thereof to a crude levocetirizine or a pharmaceutically acceptable salt thereof;

c) purification of the crude levocetirizine or the pharmaceutically acceptable salt thereof to obtain pure levocetirizine or a pharmaceutically acceptable salt thereof, optionally via formation of a solvate.

3. The process of claim 2, wherein the pure levocetirizine or the pharmaceutically acceptable salt thereof contains less than 0.2% of the intermediate of formula II.

4. The process of claim 2, wherein the aprotic solvent is acetonitrile.

5. The process of claim 1 comprising the following steps:

i) reaction of intermediate with formula II

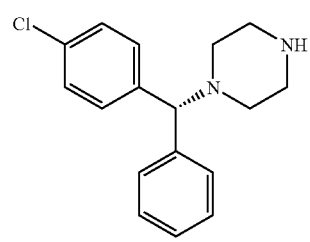

with a diglycolic acid derivative of formula

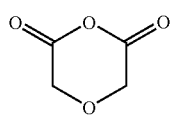

or X—CO—CH$_2$—O—CH$_2$—R, wherein X is OH or halogen group and R is COOH; COX, wherein X is halogen; COOM, wherein M is alkali or earth alkali metal or N(R$_1$)$_4$; CONH$_2$; CONR$_1$R$_2$, COOR$_1$, or CN, wherein R$_1$ and R$_2$ are independently selected from H, lower alkyl group, aryl group, to obtain intermediate of formula IV

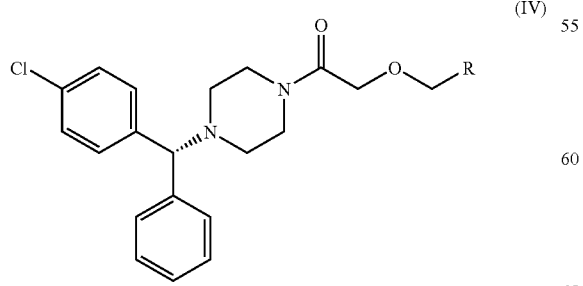

wherein R is as defined above;

ii) reducing intermediate of formula (IV) with selective reducing agent to obtain the product of formula (V)

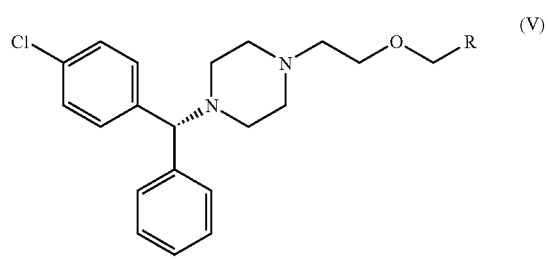

wherein R is as defined above;

iii) in case R is not COOH conversion of intermediate (V) to levocetirizine, iv) optionally conversion of levocetirizine to the pharmaceutically acceptable salt thereof.

6. The process of claim 5, wherein R of intermediate (IV) produced in step (i) is COOH, and wherein intermediate (IV) is converted to a compound of formula (IV) wherein R is a group which can be converted to COOH.

7. The process according to claim 5, wherein the selective reducing agent is selected from the group consisting of NaBH$_4$, optionally in the presence of carboxylic acids such as acetic acid, trifluoroacetic acid, formic acid or in the presence of sulfonic acids; NaBH$_3$CN, optionally in the presence of carboxylic acids such as acetic acid, propanoic acid, trifluoroacetic acid; NaBH$_3$OCOR$_3$ or NaBH(COOR$_3$)$_3$, wherein R$_3$ is methyl, trifluoromethyl and the like; boranes such as borane-solvent complexes, wherein solvent is selected from tetrahydrofurane (H$_3$B-THF), dimethyl sulfide (H$_3$B-SMe$_2$, BMS), diethyl ether (H$_3$B-diethylether); (R$_4$)$_3$OBF$_4$/NaBH$_4$ wherein R$_4$ is methyl, ethyl, propyl and the like.

8. A compound of formula (IV)

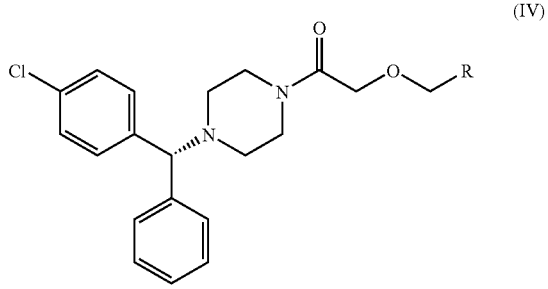

wherein R is as defined in claim 5.

9. The compound of claim 8 wherein R is COOH and which is characterized by an X-ray powder diffractogram having peaks at about: 7,1; 14,2; 16,5; 18,2; 19,2; 19,9; 21,1; and 23,1 °2Theta.

10. A process for the production of levocetirizine, or a pharmaceutically acceptable salt thereof, comprising the steps of:

a) reducing intermediate of formula (IV)

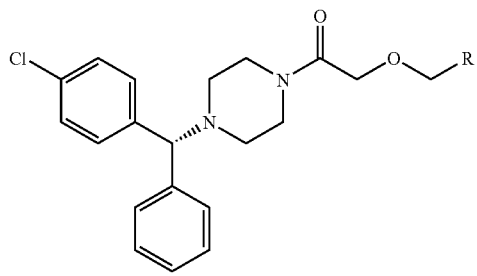

(IV)

with a selective reducing agent to obtain an intermediate of the formula (V) or a salt thereof

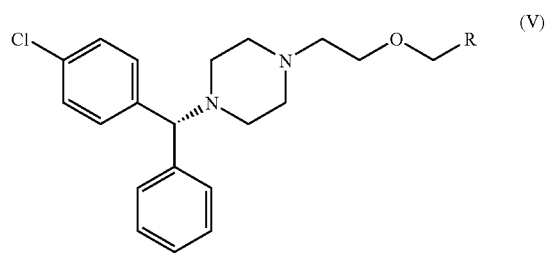

(V)

wherein R is COOH; COX, wherein X is halogen; COOM, wherein M is alkali or earth alkali metal or $N(R_1)_4$; $CONH_2$; $CONR_1R_2$, $COOR_1$, or CN, wherein $R_1$ and $R_2$ are independently selected from H, lower alkyl group, aryl group; and b) in the case in which R is not COOH conversion of intermediate (V) to levocetirizine or a pharmaceutically acceptable salt thereof.

* * * * *